US006414184B1

(12) United States Patent
Bruchmann et al.

(10) Patent No.: US 6,414,184 B1
(45) Date of Patent: Jul. 2, 2002

(54) PROCESS FOR PRODUCING POLYISOCYANATES CONTAINING BIURET GROUPS FROM (CYCLO)ALIPHATIC DIISOCYANATES

(75) Inventors: Bernd Bruchmann, Freinsheim; Martin Reif, Ludwigshafen; Werner Hofscheuer, Neuhofen; Joachim Jähme, Bobenheim-Roxheim; Werner Langer, Ludwigshafen; Hans Renz, Meckenheim; Günter Mohrhardt, Speyer; Michael Schiessl, Hassloch, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/242,288

(22) PCT Filed: Aug. 18, 1997

(86) PCT No.: PCT/EP97/04505

§ 371 (c)(1),
(2), (4) Date: Feb. 10, 1999

(87) PCT Pub. No.: WO98/07771

PCT Pub. Date: Feb. 26, 1998

(30) Foreign Application Priority Data

Aug. 19, 1996 (DE) .......................................... 196 33 404

(51) Int. Cl.⁷ .............................................. C08G 18/10
(52) U.S. Cl. ......................................... 560/335; 528/59
(58) Field of Search ............................. 560/335; 528/59

(56) References Cited

U.S. PATENT DOCUMENTS

| 3,358,010 A | 12/1967 | Britain ........................ 560/335 |
| 3,903,126 A | 9/1975 | Woerner et al. ............. 560/335 |
| 4,147,714 A | 4/1979 | Hetzel et al. ................ 521/162 |
| 4,264,519 A | 4/1981 | Hennig et al. .............. 560/335 |
| 4,292,255 A | 9/1981 | Hennig et al. .............. 560/335 |
| 4,613,686 A | 9/1986 | Koenig et al. .............. 560/335 |
| 4,793,112 A | 12/1988 | Suefke ......................... 52/511 |
| 4,837,359 A | 6/1989 | Woynar ........................ 560/335 |
| 5,641,851 A | 6/1997 | Wolff et al. .................. 560/335 |
| 5,955,143 A * | 9/1999 | Wheatley et al. ........... 424/501 |

FOREIGN PATENT DOCUMENTS

| DE | 2 261 065 | 6/1974 |
| DE | 26 09 995 | 9/1977 |
| DE | 34 03 277 | 8/1986 |
| DE | 195 25 474 | 1/1997 |
| EP | 003 505 | 8/1979 |
| EP | 277 353 | 8/1988 |
| EP | 716 080 | 6/1996 |

OTHER PUBLICATIONS

J. prak. Chem. 336 (1994), S. 185–200.

* cited by examiner

*Primary Examiner*—Rachel Gorr
(74) *Attorney, Agent, or Firm*—Keil & Weinkauf

(57) ABSTRACT

A process for preparing biuret-functional polyisocyanates from at least one aliphatic or cycloaliphatic diisocyanate and from at least one amine or water or a mixture thereof as reactants involves mixing the reactants with one another in a mixing unit having a high shear action.

12 Claims, 1 Drawing Sheet

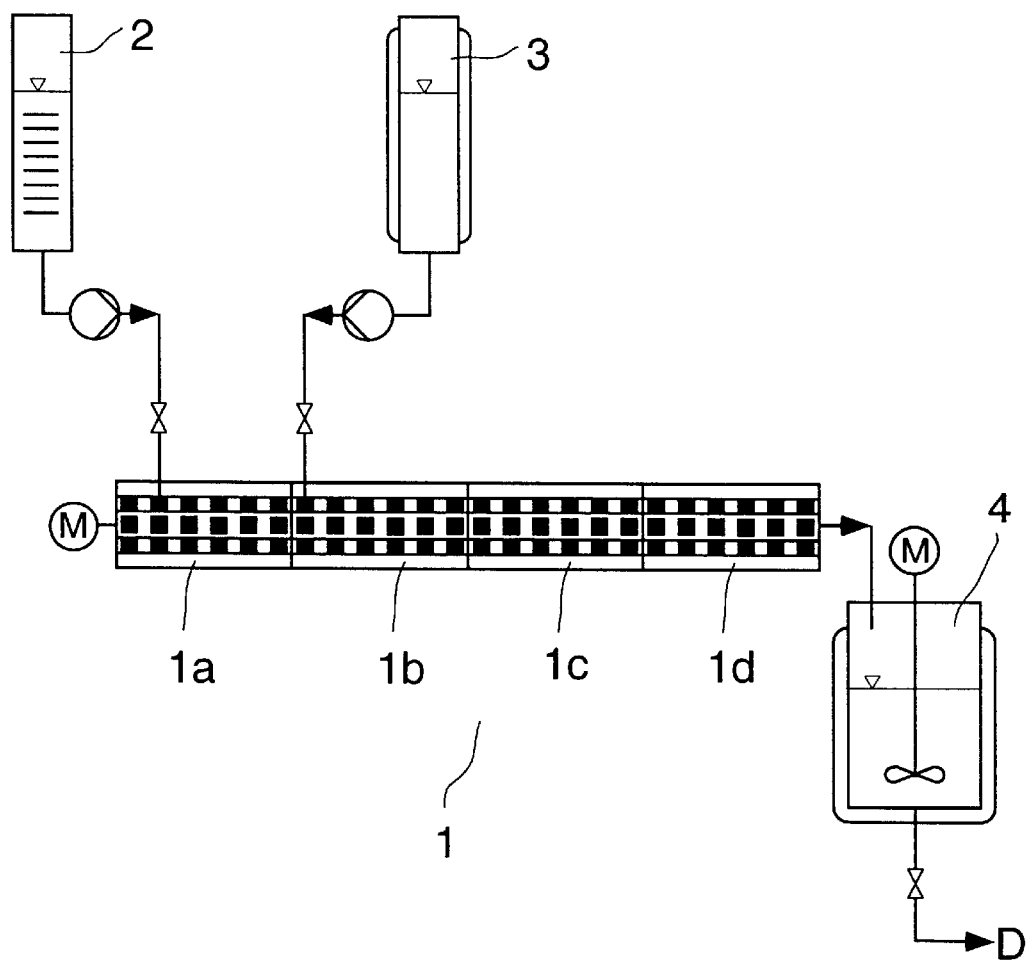

PROCESS FOR PRODUCING POLYISOCYANATES CONTAINING BIURET GROUPS FROM (CYCLO)ALIPHATIC DIISOCYANATES

The invention relates to a process for preparing biuret-functional polyisocyanates from (cyclo)aliphatic diisocyanates and at least one amine or water or a mixture thereof, together if desired with at least one alcohol, as reactants which are mixed with one another in a mixing unit having a high shear action. Biuret-functional (cyclo)aliphatic polyisocyanates are employed, inter alia, in high-grade light-stable and weather-resistant two-component PU coating materials, and in adhesives and dispersions. To prepare biurets, a defined amount of a biuretizing agent, for example water, water donors, amines or ureas, is added to the diisocyanates, and these compounds are reacted at, normally, from 100 to 200° C. The excess isocyanate monomer is subsequently separated off by single-stage or multi-stage distillation. A good review of the various options for preparing biurets is given, inter alia, by DE-A 34 03 277, EP-A 0 716 080, DE 195 25 474.0, and by a review article in J. prakt. Chem. 336 (1994), 185–200.

The literature has already disclosed processes for the direct preparation of biurets from isocyanates and amines.

For example, DE-A 22 61 065 describes, inter alia (Example 16), the reaction of excess amounts of 1,6-hexamethylene diisocyanate (HDI) with 1,6hexamethylenediamine (HDA). According to this Example, the reactants are stirred at 180° C. for 12 hours. This long period of subsequent heating at a high temperature not only is extremely uneconomic but leads, especially under industrial production conditions, to a discoloration of the product, so that its use in lightfast coating materials is greatly restricted. Reworking of the above-mentioned Example 16 gave a highly viscous biuret with a considerable proportion of solids. It is therefore not possible to use the process described there to obtain a biuret polyisocyanate which is free from monomeric starting diisocyanate and is also completely free from insoluble, gel-like by-products.

DE-A 26 09 995 attempts to circumvent the disadvantages of the formation of solids in DE-A 22 61 065 by introducing the amines in gaseous form, at from 100 to 250° C., into the initial charge of diisocyanate. As a result of the in all cases high dilution of the diamines introduced in gaseous form, instances of precipitation of polyurea occur to a much less extent, although even here it is impossible to avoid completely the formation of urea agglomerates, since they form by local overconcentration of the reactants on the nozzle itself, thereby blocking it. In addition, owing to the use of gaseous diamines, large volumes are required to perform this process on the industrial scale, thereby making it difficult to control the reaction conditions.

EP-B 0 003 505 attempts to circumvent the problem of nozzle blockage by injecting the amine into the initial charge of isocyanate through a smooth-jet nozzle under high pressure ($2 \cdot 10^5$ to $1 \cdot 10^8$ Pa) at from –20 to 250° C.

In the process described in EP-B 0 277 353, the formation of solids is avoided by combining the amines, with or without the addition of water or alcohols, with the isocyanate through nozzles in a mixing chamber at above 250° C. and at pressures of up to $1 \cdot 10^7$ Pa. After-reaction to adjust the molecular weight distribution takes place subsequently in a stirred vessel at from 80 to 220° C. A process of this kind is technologically expensive owing to the high pressures and the nozzle technology. In the downstream reactors, however, the formation of solids may still be a problem. The high temperatures of more than 250° C. are already close to the decomposition point of HDI, for example, so that it is not possible to rule out thermal damage to the product, which is manifest in a dark coloration.

As is evident from the above, using the processes described to date it is possible only with extreme difficulty to prepare virtually colorless, biuret-functional polyisocyanates without the concomitant formation of large amounts of disruptive solids. Since biuret-functional diisocyanates are preferentially employed in the clearcoat sector, discoloration and a high solids content in these isocyanates are disadvantageous. Many of the above-described processes, furthermore, can be operated under industrial production conditions only at great technological expense.

It is an object of the present invention, therefore, to provide a process for preparing biuret-functional polyisocyanates which is free from the disadvantages described above.

We have found that this object is achieved, surprisingly, in that biuret-functional polyisocyanates with commercial viscosities of from 3000 to 10,000 mPas and good color numbers of 500 Hz or less, preferably 300 Hz or less, in particular 100 or less, can be produced under moderate conditions by mixing an aliphatic, cycloaliphatic or araliphatic diisocyanate and at least one amine or water, or a mixture thereof and, if desired, an alcohol and bringing them into contact with one another in a mixing unit having a high shear action.

The present invention accordingly provides a process for preparing biuret-functional polyisocyanates from at least one aliphatic, cycloaliphatic or araliphatic diisocyanate or a mixture of two or more thereof and at least one amine or water or a mixture of two or more thereof as reactants, which comprises mixing the reactants with one another in a mixing unit having a high shear action.

Furthermore, the present invention relates to a biuret-functional polyisocyanate preparable by a process for preparing a biuret-functional polyisocyanate from at least one aliphatic or cycloaliphatic or araliphatic diisocyanate or a mixture of two or more thereof and at least one amine or water or a mixture of water and at least one amine as reactants, in which the reactants are mixed with one another in a mixing unit having a high shear action and are reacted together.

The term "biuret-functional polyisocyanate" as used in the context of the present invention relates to polyisocyanates, as defined within the context of the present invention, which as principal component comprise molecules with the formula

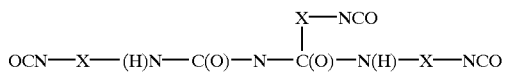

and homologous isomers thereof, where X is an aliphatic, cycloaliphatic or araliphatic alkylene group.

Appropriate starting products for the preparation of the biuret-functional polyisocyanates are the aliphatic, cycloaliphatic or araliphatic diisocyanates which are known per se, individually or in mixtures of two or more thereof. These are preferably alkylene diisocyanates having 4 to 12 carbon atoms in the alkylene radical, such as 1,4-tetramethylene diisocyanate, 1,6-hexamethylene diisocyanate (HDI), 1,12-dodecamethylene diisocyanate, 2ethyltetramethylene 1,4-diisocyanate, 2-methylpentamethylene 1,5-diisocyanate, 2,2,4-trimethylhexamethylene 1,6-diisocyanate,2,4,4-trimethylhexamethylene 1,6-diisocyanate and lysine alkyl ester diisocyanates;

cycloaliphatic diisocyanates, such as cyclohexane 1,3- and 1,4-diisocyanate, isophorone diisocyanate (IPDI) and bis(4-isocyanatocyclohexyl)methane, 2,5- and 2,6-diisocyanatomethylnorbornane, or araliphatic diisocyanates, such as xylylene diisocyanate and tetramethylxylylene diisocyanate, with particular preference being given to the use of 2-butyl-2-ethylpentamethylene diisocyanate, 2methylpentamethylene diisocyanate, IPDI, HDI and bis(4-isocyanatocyclohexyl)methane.

Further starting materials for the process according to the invention are organic mono- and diamines having aliphatically and/or cycloaliphatically attached primary or secondary amino groups. These include, for example, aliphatic or cycloaliphatic monoamines of the formula R—NH$_2$ where R is an aliphatic hydrocarbon radical of 1 to 12 carbon atoms or a cycloaliphatic hydrocarbon radical of 5 to 7 carbon atoms, such as, for example, methylamine, n-butylamine, n-dodecylamine, cyclopentylamine, cyclohexylamine or cycloheptylamine. Ammonia can also be considered.

Mention may also be made of diamines, containing primary amino groups, of the formula R'(NH$_2$)$_2$ where R' is an aliphatic hydrocarbon radical of 2 to 12 carbon atoms or a cycloaliphatic hydrocarbon radical of 4 to 17 carbon atoms. Examples which may be mentioned here are ethylenediamine, 1,2- and 1,3-propylenediamine, 1,4-diaminobutane, 2,2dimethythylpropane-1,3-diamine, 1,6-hexamethylenediamine, 2,5-dimethylhexane-2,5-diamine, 2,2,4-trimethylhexane-1,6-diamine, 1,8-diaminooctane, 1,10-diaminodecane, 1,11-undecanediamine, 1,1 2-dodecanediamine, 1methyl-4-aminoisopropylcyclohexyl-1-amine, 3-aminomethyl-3,5,5-trimethylcyclohexyl-1-amine, 1,2-bis(aminomethyl)cyclobutane, 1,2- and 1,4-diaminocyclohexane, 1,2- and 1,4-,1,5- and 1,8-diaminodecalin, 1-methyl-4-aminoisopropylcyclohexyl-1-amine, 4,4'-diaminobicyclohexyl, bis(4-aminocyclohexyl)methane, 2,2-bis(4-aminocyclohexyl)propane, 3,3'-dimethyl-4,4'-diaminodicyclohexylmethane, 1,2-bis(4-aminocyclohexyl)-ethane, 3,3', 5,5'-tetramethylbis(4-aminocyclohexyl)methane and -propane, and isophoronediamine, and mixtures of two or more thereof.

Particularly preferred amines employed are hexamethylenediamine, isophoronediamine and bis(4-aminocyclohexyl)-methane.

In a particularly preferred embodiment of the present invention, the diisocyanate employed is hexamethylene diisocyanate and the amine employed is hexamethylenediamine.

In the process according to the invention the amines can also be employed as a blend with water and/or aliphatic alcohols, in which case tertiary alcohols in particular are employed. Examples which may be mentioned are 1,4-dihydroxybutane, neopentylglycol, trimethylolpropane, glycerol and tert-butanol, the latter being particularly preferred. It is also possible to employ water alone.

When carrying out the novel process, the starting diisocyanates and the amines, water and mixtures thereof, with or without an alcohol, are reacted in a proportion such that the ratio of equivalents of isocyanate groups to the isocyanato-reactive groups is at least 2:1, preferably from 4:1 to 25:1 and, in particular, from 7:1 to 20:1, the primary amino groups entering the calculation as difunctional groups. These reactants are introduced, preferably continuously, into the reactor in the above-mentioned proportion.

BRIEF DESCRIPTION OF THE DRAWING

The drawing is a schematic representation of one embodiment of an apparatus for carrying out the process of this invention.

It is essential to the invention that the reactants used in the present process are brought into contact with one another in a mixing unit having a high shear action.

The term "high shear action" denotes shear forces which are induced by shear rates in a range from approximately 100 to approximately 200,000 s$^{-1}$, preferably from approximately 1000 to approximately 100,000 s$^{-1}$ and, in particular, from approximately 3000 to approximately 30,000 s$^{-1}$.

In this context, the shear rate $\dot{\gamma}$ is defined as follows:

$$\dot{\gamma} = \frac{r \cdot \Omega}{b}$$

where r=radius of the rotor (mm); $\Omega$=angular velocity (s$^{-1}$); and b=gap width between rotor and stator (mm).

For producing the shear forces and the shear field, respectively described above, it is possible in principle to use all suitable mixing units. Examples which can be mentioned are suspension or dispersion apparatus consisting of rotor/stator elements and, if desired, conveying elements, with particular mention being made of ULTRA-TURRAX dispersion apparatus, intensive mixers, shear disk mixers, extruders, mills, etc. Ultrasound mixers can also be mentioned.

In the process according to the invention, the reactants are brought together in a shear field produced as set out above at from approximately 20 to approximately 280° C., preferably from approximately 80 to approximately 250° C. and, in particular, from approximately 100 to approximately 220° C., and are then reacted in a manner known per se.

In this case the diisocyanate is generally introduced as initial charge, the appropriate shear field is established, and the reactor is heated to an appropriate level. Subsequently, water, the possibly preheated monoamine or diamine, or the mixture of two or more thereof, possibly mixed with an alcohol, are added, it also being possible for a catalyst to be present, and mixed.

Following the mixing stage, or the passage through the mixing chamber and the residence time section which may possibly be included downstream of this, the reaction mixture is subsequently brought to reaction temperature, continuously or at stages, preferably within a period of less than approximately 20 minutes, more preferably in a period of approximately 10 minutes, the reaction temperature generally being from approximately 80 to approximately 250° C., preferably from approximately 100° C. to approximately 220° C., and is subjected to a thermal aftertreatment at this temperature over a period of not more than approximately 5 hours, preferably not more than approximately 2 hours.

Thermal aftertreatment can be carried out, for example, in a reactor, in a cascade of reactors, in continuous-throughflow stirred vessels, or in a tube reactor.

Following the thermal aftertreatment, the reaction product is in the form of a solution of biuret-functional polyisocyanates in excess starting diisocyanate, and this solution can be freed, directly following thermal aftertreatment or at a later point in time, from excess starting diisocyanate by means of distillation or by extraction using, for example, n-hexane.

Preferably, the entire preparation process described above is operated continuously.

In this way high-quality polyisocyanates with a biuret structure are obtainable, with a content of excess starting diisocyanate of not more than 0.5% by weight.

The biuret-functional polyisocyanates prepared in accordance with the invention are notable for good color numbers, good storage stability and good dilutability with aprotic solvents.

They can be used as a crosslinking component in light-fast and weather-resistant two-component PU coating materials and in the preparation of rigid and flexible PU foams, in adhesives and (coating) dispersions.

The Examples below serve to illustrate the present invention.

EXAMPLES

Example 1

Hexamethylene diisocyanate (HDI) (1000 g) was charged in a nitrogen atmosphere to a 2 l stirred reactor, the Ultra-Turrax was lowered and set at 9000 rpm, and the isocyanate was heated to 80° C. Hexamethylenediamine (HDA) heated to 80° C. was added within 10 minutes.

The mixture was subsequently heated to the reaction temperature indicated in Table 1, and stirring with the Turrax was continued throughout the reaction period indicated. After it had cooled, the reaction solution was distilled on a thin-film evaporator at 165° C. oil temperature and at a pressure of $2.5 \cdot 10^2$ Pa in order to remove the unreacted HDI.

TABLE 1

Reactions of HDI with HDA

| HDA [g] | Reaction temperature [° C.] | Reaction time [min] | Visc. 25° C. [mPas] | NCO [% by wt.] |
|---|---|---|---|---|
| 30 | 180 | 180 | 3250 | 22.4 |
| 40 | 210 | 30 | 4650 | 22.2 |
| 40 | 230 | 15 | 12,000 | 19.9 |

Example 2

HDI (1000 g) was charged in a nitrogen atmosphere to a 2 l stirred reactor, the Ultra-Turrax was lowered and set at 9000 rpm, and the isocyanate was heated to 80° C. Over a period of 10 minutes, hexamethylenediamine heated at 80° C., water, mixtures thereof, or the tert-butanol/HDA mixture and, if desired, catalyst were added (see Tables 2 and 3).

The Turrax was then removed and replaced by a conventional anchor agitator. The reaction mixture was then heated to the reaction temperatures indicated in Tables 2 and 3, and stirring was continued with the anchor agitator for the reaction period indicated. After it had cooled, the reaction mixture was distilled on a thin-film evaporator at 165° C. oil temperature and at a pressure of $2.5 \cdot 10^2$ Pa in order to remove the unreacted HDI.

TABLE 2

Reactions of HDI with HDA, water or HDA/water mixtures

| HDA [g] | Water [g] | Catalyst [mol % based on HDI] | Reaction temperature [° C.] | Reaction time [min] | Visc. 25° C. [mpas] | NCO [% by wt.] |
|---|---|---|---|---|---|---|
| 30 | — | — | 180 | 300 | 5310 | 21.9 |
| 20 | — | — | 190 | 300 | 4650 | 22.0 |
| — | 10 | DBP (0.2) | 150 | 60 | 3220 | 22.6 |
| 7 | 7 | DEHP (1.0) | 210 | 60 | 6430 | 21.2 |
| 15 | 5 | DEHP (1.0) | 210 | 60 | 8410 | 20.9 |

TABLE 3

Reaction of HDI with HDA/tert-butanol mixture

| HDA [g] | tert Butanol [g] | Catalyst [mol % based on HDI] | Reaction temperature [° C.] | Reaction time [min] | Visc. 25° C. [mpas] | NCO [% by wt.] |
|---|---|---|---|---|---|---|
| 7 | 27 | DEHP (1.0) | 180 | 300 | 3480 | 22.6 |

DBP = Dibutyl phosphate
DEHP = Di(2-ethylhexyl) phosphate

Example 3

HDI 2 heated at 80° C. was introduced continuously into an intensive mixer 1 consisting of four separately heatable, series connected mixing units 1a–1d (see FIG. 1) at a rotor speed of 4000 rpm. HDA heated at 80° C., water or the mixture of HDA and water 3 was metered in in the second mixing unit 1b. The residence time of the reaction mixture can be influenced by means of the volume flow, and was about 0.5–2 min. The reaction mixture passed subsequently into a heated stirred reactor 4 in which the reaction was brought to completion. The residence time here was 0.5–2 h. To separate off the unreacted, monomeric HDI, distillation was carried out in a thin-film evaporator at an oil temperature of 165° C. and a pressure of $2.5 \cdot 10^2$ Pa. The reaction data are compiled in Table 4.

TABLE 4

Data for the intensive mixer experiments

| HDI [g/h] | HDA [g/h] | Water [g/h] | Temperature of int. mixer [° C.] | Temperature of vessel [° C] | NCO biuret [%] | Visc. 25° C. [mPas] |
|---|---|---|---|---|---|---|
| 1000 | 20 | — | 180 | 190 | 21.9 | 4250 |
| 2000 | 40 | — | 180 | 210 | 21.8 | 5230 |
| 2000 | — | 20 | 150 | 150 | 22.2 | 4350 |
| 1000 | 7 | 7 | 180 | 190 | 22.0 | 4130 |

Comparative Example 1 (according to DE-A 22 61 065)

HDI (1000 g) was charged at 25° C. in a nitrogen atmosphere to a 2 l stirred reactor, and 86.3 g of hexamethylenediamine which had been heated to 70° C. were added within 25 minutes with rapid stirring, using an anchor agitator. Immediately following this addition, polymeric urea precipitated as a solid. The reaction mixture was heated to 180° C. and stirred at this temperature for 12 h. The mixture was dark in color and still contained considerable amounts of solids. Filtration gave a yellow-brown biuret with a viscosity >25,000 mPas (25° C.), which could not be distilled in the thin-film evaporator for removal of monomeric HDI.

Comparative Example 2
(with reduced proportion of HDA, similar to the Examples according to the invention in Table 2, but without the use of a high-shear mixing unit).

HDI (1000 g) was charged at 80° C. in a nitrogen atmosphere to a 2 l stirred reactor, and 20 g of hexamethylenediamine which had been heated to 80° C. were added over the course of 10 minutes with rapid stirring, using an anchor stirrer. Immediately after this addition, polymeric urea precipitated as a solid. The reaction mixture was heated to 190° C. and stirred at this temperature for 5 h. The mixture was yellow and still contained considerable amounts of solid. Filtration and distillation gave, in a yield of 10%, a biuret with a viscosity of 1190 mPas (25° C.) and an NCO content of 24.1% by weight.

We claim:

1. A process for preparing biuret-functional polyisocyanates from at least one aliphatic, cycloaliphatic or araliphatic diisocyanate or a mixture of two or more thereof and at least one amine or water or a mixture of two ore more thereof as reactants, in which the reactants are mixed with one another in a mixing unit having a high shear action which is induced by shear rates of from 100 to 200,000 $s^{-1}$ and are reacted together, and wherein the reactants are brought together in a shear field at from approximately 80 to approximately 250° C.

2. A process as claimed in claim 1, characterized in that the aliphatic, cylcloaliphatic or araliphatic diisocyanate is an alkylene diisocyanate having 4 to 12 atoms in the alkylene radical or is a mixture of two or more thereof.

3. A process as claimed in claim 1, characterized in that at least one amine, water or the mixture thereof is additionally mixed with at least one alcohol.

4. A process as claimed in claim 3, characterized in that the at least one alcohol is a tertiary alcohol.

5. A process as claimed in claim 1, characterized in that the at least one amine is hexamethylenediamine, isophoronediamine or bis(4-aminocyclohexyl)methane.

6. A process as claimed in claim 3, characterized in that the at least one amine is hexamethylenediamine, isophoronediamine or bis(4-aminocyclohexyl)methane.

7. A process as claimed in claim 1, characterized in that the isocyanate employed is hexamethylene diisocyanate and the at least one amine employed is hexamethylenediamine.

8. A process as claimed in claim 3, characterized in that the isocyanate employed is hexamethylene diisocyanate and the at least one amine employed is hexamethylenediamine.

9. A process as claimed in claim 1, characterized in that it is operated continuously.

10. A process as claimed in claim 1, wherein the reactants are stirred with a rotor.

11. A method of crosslinking components in light-fast and water-resistant two-component PU coating materials and in the preparation of rigid and flexible PU-foams, in adhesives and coating dispersions by reacting said components with a polyisocyanate made by the process of claim 1.

12. A process as claimed in claim 1, wherein the reactants are mixed with one another in a mixing unit having a high shear action which is induced by shear rates of from 1000 to 100,000 $s^{-1}$.

* * * * *